(12) United States Patent
O'Brien et al.

(10) Patent No.: US 7,387,036 B2
(45) Date of Patent: Jun. 17, 2008

(54) VESSEL WITH RETENTION FEATURES AND METHOD THEREFOR

(75) Inventors: Darin O'Brien, Winterset, IA (US); Nate Morken, Maple Grove, MN (US); Alan Wirbisky, Eden Praire, MN (US)

(73) Assignee: Gentra Systems, Inc., Minneapolis, MN (US)

( * ) Notice: Subject to any disclaimer, the term of this patent is extended or adjusted under 35 U.S.C. 154(b) by 51 days.

(21) Appl. No.: 10/827,872

(22) Filed: Apr. 20, 2004

(65) Prior Publication Data

US 2005/0229724 A1    Oct. 20, 2005

(51) Int. Cl.
*G01N 1/00*    (2006.01)
(52) U.S. Cl. .................................... 73/863.21
(58) Field of Classification Search .............. 73/28.05, 73/28.06, 863.22, 863.21, 864.91, 864.71; 422/72, 102; 220/607, 600, 671–673, 675; 494/85
See application file for complete search history.

(56) References Cited

U.S. PATENT DOCUMENTS

| | | | |
|---|---|---|---|
| 3,521,788 A * | 7/1970 | Carter et al. ................ 220/675 |
| 4,400,269 A * | 8/1983 | Gordon, Jr. ................. 209/447 |
| 4,425,368 A * | 1/1984 | Watkins ....................... 426/107 |
| 4,881,656 A * | 11/1989 | Chumley et al. ........... 220/270 |
| 5,234,667 A | 8/1993 | Radtke et al. .............. 422/102 |
| 5,343,767 A * | 9/1994 | Marple et al. ........... 73/863.22 |
| 5,788,293 A * | 8/1998 | Krenzler ..................... 209/434 |
| 6,102,211 A * | 8/2000 | Krenzler ..................... 209/434 |
| 6,134,835 A * | 10/2000 | Krupke et al. ................ 49/200 |
| 6,363,800 B1 * | 4/2002 | Call et al. ................ 73/863.22 |
| D475,727 S * | 6/2003 | Kelava ....................... D15/147 |
| 2005/0153025 A1* | 7/2005 | Hopkins ..................... 426/107 |

FOREIGN PATENT DOCUMENTS

JP          11-208738    * 11/1999
WO       WO-01/28680 A2    4/2001

OTHER PUBLICATIONS

"Hi-Yield Nucleic Acid Recovery Tubes", *Robbins Scientific*, http://www.robsci.com/PCR/ThinWall_Hi-Yield.html, (2003), 1 page.

* cited by examiner

*Primary Examiner*—Robert Raevis
(74) *Attorney, Agent, or Firm*—Schwegman, Lundberg & Woessner, P.A.

(57) ABSTRACT

A vessel with retention features for the retention of pellets for use in laboratory processes, manufacturing, and producing packaged foods, chemicals, and medicines.

21 Claims, 3 Drawing Sheets

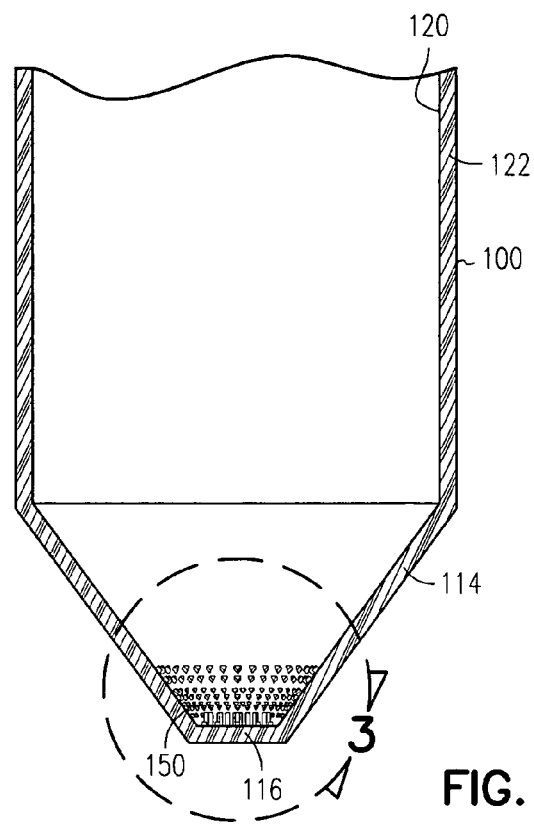
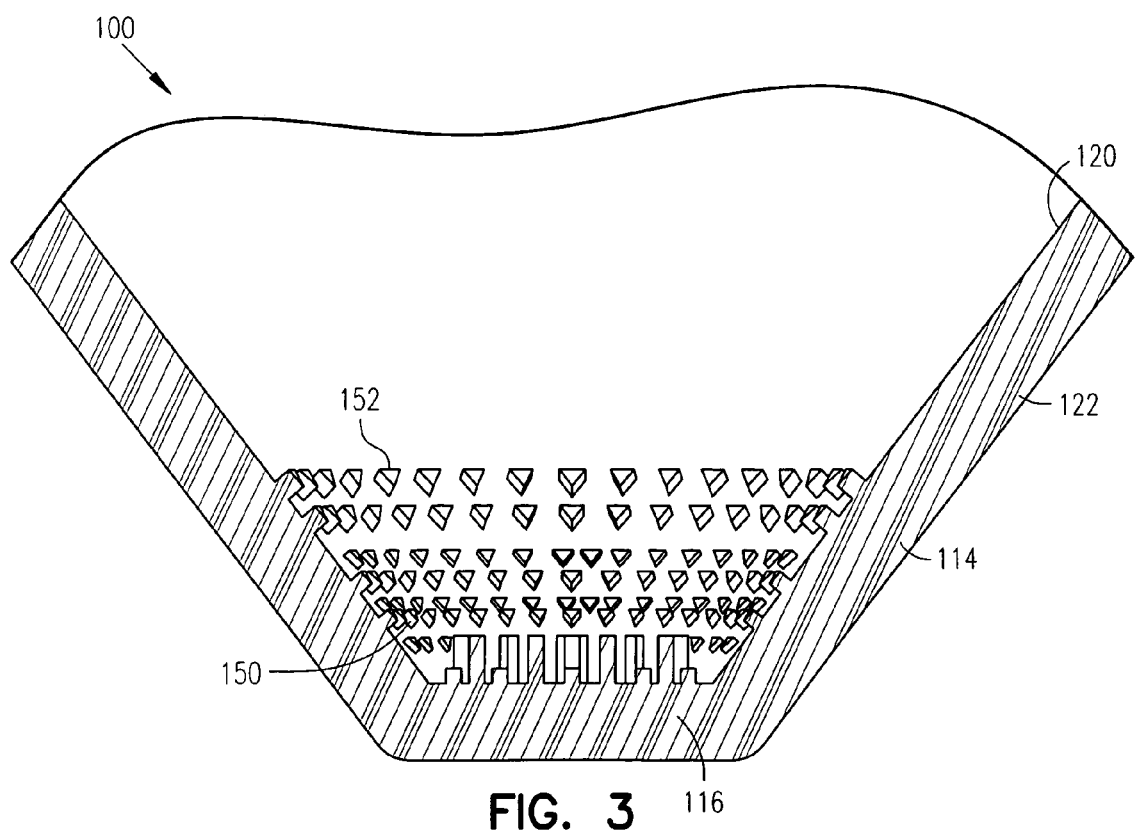

VESSEL WITH RETENTION FEATURES AND METHOD THEREFOR

FIELD

The present relates generally to vessels, such as centrifuge tubes, with sample retention features.

BACKGROUND

Samples, such as material containing DNA, are currently processed both manually and automatically in vessels, such as centrifuge tubes. In many lab processes, a sample of some material which contains components to be isolated, mixed, or the like is typically placed in a sample vessel.

Typical lab procedures for working with samples include mixing and agitating the sample, adding material to the sample, removing material from the sample by pouring, and the like. These processes have traditionally been performed by hand. However, some methods of isolating components involve automated methods.

Some laboratory procedures require the user or the machine to pour-off a portion of the mixture and retain the other portion, for example a supernatant is poured off and one or more pellets are retained for further processing. This pour-off process can be very delicate, and if not done carefully, can result in lost pellets. In the case of unique or limited samples, or samples which require long development cycles, such errors can be devastating when the samples cannot be duplicated, or are irreplaceable. This is especially true for automated methods, as such pour-off techniques can be performed more delicately by humans than by machines.

Furthermore, during precise laboratory procedures, such as DNA or RNA isolation, pellet loss can also cause contamination and cross-contamination of samples and the laboratory, such that the entire process needs to be restarted.

One approach in facilitating pellet retention is shown in U.S. Pat. No. 5,234,667, which includes a micropitted roughened portion within a micro-centrifuge tube. However, this approach as described by Radtke et al. is intended for μL-sized samples and is not scalable for use with 1 mL or larger samples, and still results in pellet loss. See Example 1 described further below.

Accordingly, what is needed is a process and vessel which prevents inadvertent loss of samples during processing, such as during the pour off process.

SUMMARY

A collection device with sample retention features is provided. The collection device includes a container, for example a tubular container, having an open end, where the container is defined in part by an inner surface and an outer surface. The container is adapted to receive a mixture of substances, where the mixture includes a desired sample material. One or more retention projections are disposed on the inner surface of the container, and the one or more retention projections extend out from the inner surface of the container. The one or more retention projections adapted to retain the desired sample material within the container, for example, retaining pellets during the pour off process.

"Desired sample" relates to the portion of a mixture to be retained, for example pellet material. The pellet can be retained, for instance, when a supernatant is poured-off and thrown away, for example as in the case of biological samples, such as DNA. It is not necessary that the pellet portion be ultimately kept, however. In fact, it is possible that the pellet is the "throw-away" portion. The pellet can be retained and the tube containing the pellet thrown away, while the supernatant is poured off and collected. This may be the case in some food applications.

Several options for the container are as follows. For example, in one option, a plurality of retention projections are disposed on the inner surface, and optionally the one or more retention projections have a side surface with at least one substantially flat side surface, such as a triangular cross-sectional shape. In another option, the one or more retention features have varying height, and can be randomly spaced, or spaced in a predetermined pattern. In another option, the container includes a conical shaped portion and/or a generally flat end portion, and the one or more retention projections are disposed along the conical shape, and/or the flat end portion.

A method of collecting a desired sample is further provided herein. The method includes disposing a mixture of substances, the mixture including a desired sample material within a container. The container extends from a first open end to a second closed end, and the container is defined in part by an inner surface and an outer surface. One or more retention projections are disposed on the inner surface of the container, where the one or more retention projections extend outward from the inner surface and are adapted to retain the desired sample material within the container. The method further includes pouring the first substance from the first open end of the container, and retaining the desired sample material with the one or more retention projections.

Several options exist for the method. For example, in one option, retaining the desired sample material includes retaining the desired sample material with retention projections having a triangular cross-section, or retaining the one or more samples includes retaining the desired sample material with retention projections having at least one substantially flat side surface. In another option, retaining the one or more samples includes retaining the one or more samples with groups of retention projections that are spaced apart from each other. The method further includes, in one option, centrifuging the container prior to pouring the mixture from the first open end of the container.

In another embodiment, a method of forming a vessel is provided herein. The method includes providing a vessel with an open portion and a closed portion, where the vessel defined in part by an inner surface and an outer surface. The method further includes forming one or more retention projections on the inner surface of the vessel, and projecting the one or more retention projections out from the inner surface of the vessel.

Several options for the method are as follows. For example, in one option, forming the one or more retention projections includes forming at least a first retention projection and a second retention projection, and forming the first retention projection with a different height than the second retention projection. In another option, forming the one or more retention projections includes forming at least one substantially flat side surface on at least one of the one or more retention projections, for example the one or more retention projections are formed with a triangular cross-section. In another option, the vessel is provided with a conical portion and/or a flat end portion, and the method includes forming the one or more retention projections on or along the conical portion and/or the flat end portion.

The embodiments of the present application overcomes the shortcomings of conventional designs by providing a vessel with superior pellet retention, as to prevent loss of a pellet in laboratory processes, manufacturing, producing packaged foods, chemicals, medicines, and so forth.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

BRIEF DESCRIPTION OF THE DRAWINGS

FIG. 2 illustrates a cross-sectional view taken along 2-2 of FIG. 1.

FIG. 3 illustrates a detail view of FIG. 2.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
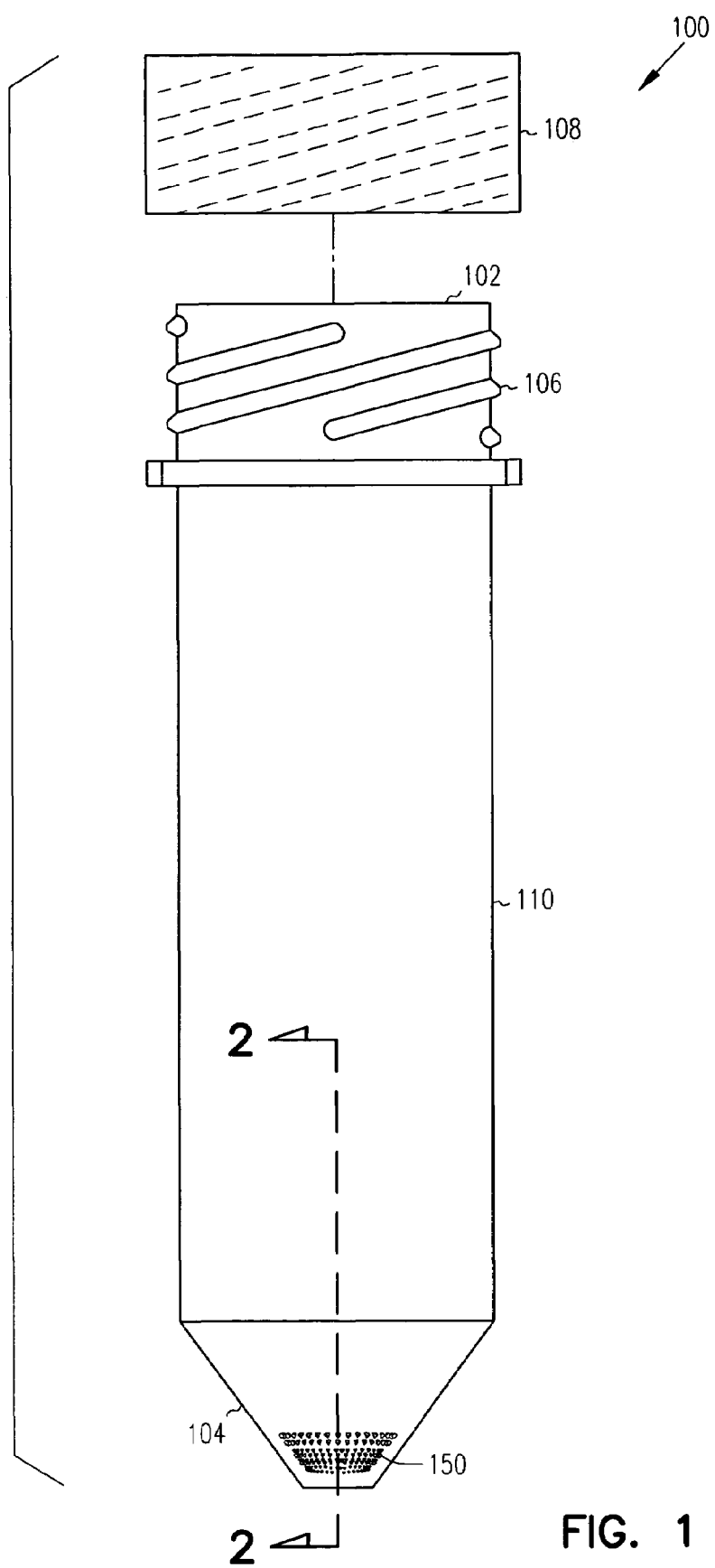
FIG. 1 illustrates a side elevational view of a collection device ted in accordance with one embodiment.

FIG. 1 illustrates a collection device 100 with pellet retention features 150. The collection device 100, in one option, is an elongate tubular structure 110 that allows for samples to be separated from mixture material, for example, by centrifuge. Examples of materials used with the collection device 100 include, but are not limited to, RNA, DNA, etc.

In one option, the collection device 100 can be formed by injection molding plastic, and includes an elongate tube with features that allow for use with other handling equipment or automated handling equipment, such as a flange on the tube. Although not so limited, one example of tube size is a tube capable of containing up to 50 ml of material. The collection device 110 forms a container or a vessel that includes a first open end 102 and a second closed end 104. Mixture of material is disposed within the first open end 102 and held within the container, formed by the collection device 100. The collection device 110 can have a variety of shapes and cross-sections. In one option, the collection device 110 is an elongate tubular structure. In another option, the collection device 110 includes a conical shape 114 in proximity to the second closed end 104. Furthermore, the collection device 110 optionally includes a flat end portion 116 at the second closed end 104.

In one option, disposed near the first open end 102 is one or more coupling features that allow for a cap 108 to be coupled over the first open end 102. In one option, the first open end includes a threaded portion 106 allowing for the cap 108 to be threadingly coupled thereto. It should be noted that other types of caps can be coupled to the first open end, such as, but not limited to, caps formed of a variety of materials or caps having a variety of coupling features, for example an interference fit or a snap fit. In one option, the cap 108 has an outer surface with one or more planar surfaces. For example, in one option, the outer cross-section of the cap 108 has a square shape.

Figure 4:
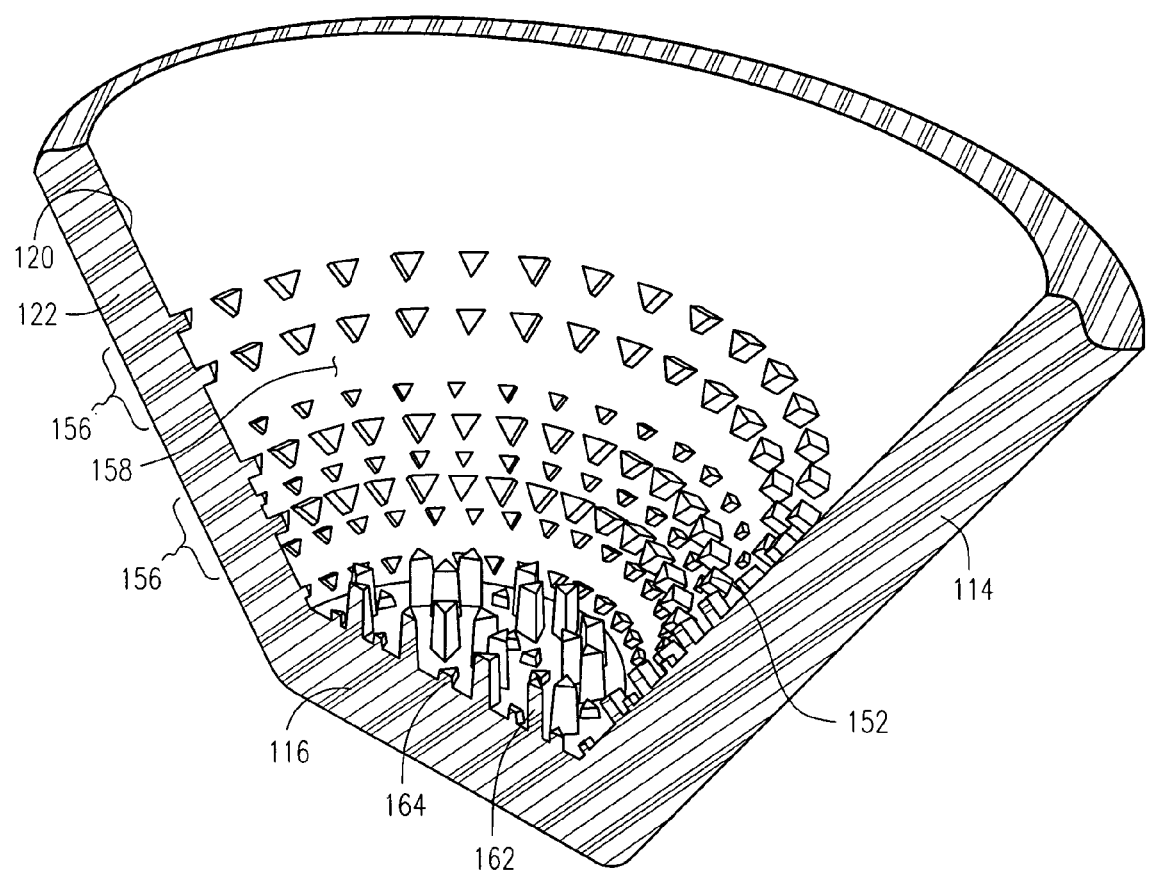
FIG. 4 illustrates a side perspective view of a portion of the on device constructed in accordance with one embodiment.

FIGS. 2-4 illustrate the collection device 100 in greater detail. The collection device 100 is defined in part by an inner surface 120 and an outer surface 122. As mentioned above, the collection device 100 includes pellet retention features 150. In one option, the pellet retention features 150 include one or more retention projections 152 disposed along the inner surface 120, where the one or more retention projections are adapted to retain sample material, such as pellets, within the container, for example when the container is manipulated during the pour off process, or when the container is inverted.

In one option, "desired sample" relates to the portion of a mixture to be retained, for example pellet material. The pellet can be retained, for instance, when a supernatant is poured-off and thrown away, for example as in the case of biological samples, such as DNA. It is not necessary that the pellet portion be ultimately kept, however. In fact, it is possible that the pellet is the "throw-away" portion. The pellet can be retained and the tube containing the pellet thrown away, while the supernatant is poured off and collected. This may be the case in some food applications.

The one or more retention projections 152 extend outward from the inner surface 120 of the collection device 100. The one or more retention projections 152 can be spaced along the inner surface 120 in a number of manners. In one option, a plurality of retention projections 154 is disposed along, for example on, the inner surface 120. The retention projections 152 can be disposed along the conical shape 114 and/or the flat end portion 116 of the collection device 100.

In another option, two or more groups 156 of retention projections 152 are disposed along the inner surface 120. The two or more groups 156 are spaced apart from one another, as illustrated in FIG. 4, by a spacing 158. In another option, the one or more retention projections 152 are randomly spaced as to create an absence of evenly spaced channels formed between the one or more retention projections 152. For example, eliminating the channels can be accomplished by varying the position of the retention projections 152 by 0.005 inches.

The one or more retention projections 152 have a variety of shapes, sizes, spacing, and orientation. For example, in one option, the one or more retention projections 152 include at least one substantially flat side surface 160, with similar or varying orientation of the retention projections 152. In another option, the one or more retention projections 152 have a triangular cross-section, such as an equilateral triangle. In yet another option, the one or more retention projections 152 have a varying height. For example, the one or more retention projections 152 include a first retention projection 162 and a second retention projection 164, where the height of the first retention projection 162 is different than the height of the second retention projection 164, as illustrated in FIG. 4. The height of the retention projections can include, but are not necessarily limited to, a first set of projections varying between 0.004-0.010 inches in height, and a second set of projections varying between 0.010-0.025 inches in height. For example, in a tube with a flat bottom, the first set of projections can be disposed along the inner surface toward the bottom and the second set of projections can be disposed on the flat bottom of the tube.

A method of collecting a sample is further provided herein. The method includes disposing a mixture, including a desired sample material, within a container. The container can include any one of the above-discussed containers, and further any of the containers illustrated in the Figures. In one option, the container extends from a first open end to a second closed end, and the container is defined in part by an inner surface and an outer surface. One or more retention projections are disposed along the inner surface of the container, where the one or more retention projections extend outward from the inner surface and are adapted to retain samples disposed within the container.

The method further includes pouring the mixture from the first open end of the container, and retaining the desired sample material, such as pellets, with the one or more retention projections. To pour the mixture from the first open end of the container, the user may use a pour-off technique. Alternatively, the container may be placed in automated machinery for processing. The method provides for pour-off without pellet loss when performed by either human or machine.

Several options are available for the method. For example, in one option, retaining the desired sample material includes retaining the desired sample material with retention projections having a triangular cross-section, or retaining the desired sample material s includes retaining the desired sample material with retention projections having at least one substantially flat side surface. In another option, retaining the desired sample includes retaining the desired sample material with groups of retention projections that are spaced apart from each other. The method further includes, in one option, centrifuging the container prior to pouring the mixture from the first open end of the container.

In another embodiment, a method of forming a vessel is provided herein. The method includes providing a vessel with an open portion and a closed portion, where the vessel defined in part by an inner surface and an outer surface. The method further includes forming one or more retention projections on the inner surface of the vessel toward the closed end, and projecting the one or more retention projections out from the inner surface of the vessel. The vessel is formed, for example, by injection molding the part in plastic. A core pin is used with shaped members of material removed from the core pin. For example, the shaped members form recesses with at least one planar surface on the core pin, and one example includes a shape member with a triangular shaped cross-section.

Several options for the method are as follows. For example, in one option, forming the one or more retention projections includes forming at least a first retention projection and a second retention projection, and forming the first retention projection with a different height than the second retention projection. The height of the retention projections can include, but are not necessarily limited to, a first set of projections 0.004-0.010 inches in height, and a second set of projections about 0.010-0.25 inches in height. In another option, forming the one or more retention projections includes forming at least one substantially flat side surface on at least one of the one or more retention projections, for example the one or more retention projections are formed with a triangular cross-section. In another option, the vessel is provided with a conical portion and/or a flat end portion, and the method includes forming the one or more retention projections on or along the conical portion and/or the flat end portion, as illustrated in FIG. 4.

The following illustrates one example of use of the device. However, the following example is illustrative of the device, but not restrictive.

EXAMPLE 1

Experiment to determine the pellet loss rates using various known methods compared with the apparatus and methods of the device herein:

50 mL Qube® brand centrifuge tubes (Gentra Systems, Inc.) were modified by 1 of 3 techniques:

(1) Micropitted tubes were made by modifying the injection mold tool core pin used to mold the Qubes® tubes. A standard molded part texture was applied to the tip of the core pin. Upon molding the part, the pits are then transferred onto the plastic surface of the tube. The texture chosen was from Mold-Tech® Standex Engraving Group standards. In this process, chemical etching produces a defined series of micropits to the core pin.

(2) Painted surface tubes were made by: Mixing 20 ml of Sherwin Williams "Illusions" Oil Based Clear Faux Glazing Liquid with 2.5-3.0 G of H&C Sharkgrip Slip-Resistant Additive and then painting the inside tip of each 50 ml Qube® by hand using a #2 artist's brush.

(3) Tubes were made in accordance with one embodiment of the collection device described herein by modifying an injection mold tool core pin to introduce the small triangular retention projections into the tip of the core pin. The desired projections on the bottom of the tube were large enough to be created using standard mold-making technique called EDM. In this case, the geometry of the projections was cut into the tip of the core pin per the requirements of the design. Upon molding the part, the projections are created as the molten plastic fills the triangular cuts in the tip surface.

| Texture | Slip rate | Number of samples |
|---|---|---|
| Standard Untextured Tubes: | ~2.5–4% | (thousands) |
| Micropitted Tubes (Scripps) | 2.27% | (4/176) |
| Painted Surface: | 0% | (0/32) |
| The collection device: | 0% | (>0/1088) |

In some cases these rates are based on small numbers, but additional tests were performed that showed the increased adhesion capability of the surface of the device. These tests usually take the form of repeated tipping of tubes with a DNA pellet in alcohol. The greater the adhesion capability, the more times a tube can be tipped without loss or movement of the DNA pellet.

The painted surface showed a 0% pellet slip rate, comparable to the tubular device described here; however, such painted surface coatings are not acceptable in an application where chemicals can contaminate the sample, such as food and biological applications. The collection device showed superior pellet retention and can be safely used for any application.

Advantageously, the vessel is an effective way to retain pellets, and prevents pellet loss associated with conventional designs. For example, in a study of 544 samples using the design discussed above, there were no lost pellets as compared with conventional designs and methods Furthermore, standard techniques, such as the pour-off process can be used by both humans and automated machines and few or no pellets will be lost, saving time and money for the user.

It is to be understood that the above description is intended to be illustrative, and not restrictive. Many other embodiments will be apparent to those of skill in the art upon reviewing the above description. The scope should, therefore, be determined with reference to the appended claims, along with the full scope of equivalents to which such claims are entitled.

What is claimed is:

1. A collection device comprising:
an elongate tubular container having an open end, the container defined in part by an inner surface and an outer surface, the container adapted to receive a mixture of substances, the mixture including a desired sample material;
one or more retention projections disposed along the inner surface of the container, the one or more retention projections extending out from the inner surface of the container, the one or more retention projections adapted to retain the desired sample material within the container; and
the one or more retention projections include two or more retention projections defined by a height, including a first projection with a first height and a second projection having a second height, and the first height is different than the second height.

2. The collection device as recited in claim 1, wherein a plurality of retention projections are disposed on the inner surface.

3. The collection device as recited in claim 1, wherein the one or more retention projections have a triangular cross-sectional shape.

4. The collection device as recited in claim 1, wherein the one or more retention projections include at least one substantially flat side surface.

5. A collection device comprising:
an elongate tubular container extending from a first open end to a second closed end, the tubular container defined in part by an inner surface and an outer surface;
one or more retention projections disposed adjacent to the second closed end of the container, the one or more retention projections disposed on the inner surface of the container and extending outward from the inner surface, the one or more retention projections adapted to retain a desired sample material within the container; and
the one or more retention projections include two or more retention projections defined by a height, including a first projection with a first height and a second projection having a second height, and the first height is different than the second height.

6. The collection device as recited in claim 5, wherein the one or more retention projections include groups of retention projections, wherein the groups of retention projections are spaced apart from one another.

7. The collection device as recited in claim 5, wherein the second closed end has a generally conical shape and the one or more retention projections are disposed within the conical shape.

8. The collection device as recited in claim 7, wherein the generally conical shape includes a generally flat end portion, and the one or more retention projections are disposed on the generally flat end portion.

9. The collection device as recited in claim 5, wherein the one or more retention projections include at least one substantially flat side surface.

10. A method of collecting a sample comprising:
disposing a mixture including a desired sample material within an elongate tubular container, the container extending from a first open end to a second closed end, the container defined in part by an inner surface and an outer surface, one or more retention projections disposed on the inner surface of the container, the one or more retention projections extending outward from the inner surface and are adapted to retain the desired sample material disposed within the container;
pouring the mixture from the first open end of the container; and
retaining the desired sample material with the one or more retention projections.

11. The method as recited in claim 10, wherein retaining the desired sample material includes retaining the desired sample material with retention projections having a triangular cross-section.

12. The method as recited in claim 10, further comprising centrifuging the container prior to pouring the mixture from the first open end of the container.

13. The method as recited in claim 10, wherein retaining the desired sample material includes retaining the desired sample material with retention projections having at least one substantially flat side surface.

14. The method as recited in claim 10, wherein retaining the desired sample material includes retaining the desired sample material with groups of retention projections that are spaced apart from each other.

15. A method of forming a vessel comprising:
forming an elongate, tubular vessel with an open portion and a closed portion, the vessel defined in part by an inner surface and an outer surface; and
forming one or more retention projections on the inner surface of the vessel, including projecting the one or more retention projections out from the inner surface of the vessel, including forming at least a first retention projection and a second retention projection, and forming the first retention projection with a different height than the second retention projection.

16. The method as recited in claim 15, wherein forming the one or more retention projections includes forming at least one substantially flat side surface on at least one of the one or more retention projections.

17. The method as recited in claim 15, wherein forming the one or more retention projections includes forming the one or more retention projections on a conical portion of the vessel adjacent the closed portion of the vessel.

18. The method as recited in claim 15, wherein forming the one or more retention projections includes forming the one or more retention projections on a substantially flat end portion of the vessel adjacent the closed portion of the vessel.

19. The method as recited in claim 15, wherein forming the one or more retention projections includes forming groups of retention projections, and spacing the groups of retention projections apart from one another.

20. A collection device comprising:
a tubular container extending from a first open end to a second closed end, the tubular container defined in part by an inner surface and an outer surface; and
one or more retention projections disposed adjacent to the second closed end of the container, the one or more retention projections disposed on the inner surface of the container and extending outward from the inner surface, wherein the one or more retention projections include two or more retention projections defined by a height, including a first projection with a first height and a second projection having a second height, and the first height is different than the second height.

21. A method of collecting a sample comprising:
disposing a mixture including a desired sample material within a container, the container extending from a first open end to a second closed end, the container defined in part by an inner surface and an outer surface, one or more retention projections disposed on the inner surface of the container, the one or more retention projections extending outward from the inner surface and are adapted to retain the desired sample material disposed within the container;

centrifuging the container;

pouring the mixture from the first open end of the container after centrifuging the container; and retaining the desired sample material with the one or more retention projections.

* * * * *